(12) United States Patent
van den Engh

(10) Patent No.: US 9,453,789 B2
(45) Date of Patent: Sep. 27, 2016

(54) CELL SORTER SYSTEM AND METHOD

(71) Applicant: Becton, Dickinson and Company, Franklin Lakes, NJ (US)

(72) Inventor: Ger van den Engh, Seattle, WA (US)

(73) Assignee: Becton, Dickinson and Company, Franklin Lakes, NJ (US)

( * ) Notice: Subject to any disclaimer, the term of this patent is extended or adjusted under 35 U.S.C. 154(b) by 0 days.

(21) Appl. No.: 14/923,289

(22) Filed: Oct. 26, 2015

(65) Prior Publication Data

US 2016/0041082 A1 Feb. 11, 2016

Related U.S. Application Data

(62) Division of application No. 14/009,032, filed as application No. PCT/US2012/028951 on Mar. 13, 2012, now Pat. No. 9,200,334.

(60) Provisional application No. 61/480,872, filed on Apr. 29, 2011.

(51) Int. Cl.
| | |
|---|---|
| *G01N 15/14* | (2006.01) |
| *C12M 1/00* | (2006.01) |
| *C12N 13/00* | (2006.01) |
| *C12Q 3/00* | (2006.01) |
| *G01N 15/10* | (2006.01) |
| *B01L 3/00* | (2006.01) |
| *G01N 15/00* | (2006.01) |

(52) U.S. Cl.
CPC ............. *G01N 15/14* (2013.01); *C12M 47/04* (2013.01); *C12N 13/00* (2013.01); *C12Q 3/00* (2013.01); *G01N 15/1012* (2013.01); *B01L 3/502715* (2013.01); *G01N 15/1031* (2013.01); *G01N 2015/0065* (2013.01); *G01N 2015/1006* (2013.01); *G01N 2015/1081* (2013.01); *G01N 2015/149* (2013.01)

(58) Field of Classification Search
None
See application file for complete search history.

(56) References Cited

U.S. PATENT DOCUMENTS

| | | | |
|---|---|---|---|
| 3,775,058 | A | 11/1973 | Bush |
| 3,791,517 | A | 2/1974 | Friedman |

(Continued)

FOREIGN PATENT DOCUMENTS

| | | |
|---|---|---|
| EP | 0154687 A2 | 9/1985 |
| JP | 2-31164 A | 2/1990 |

(Continued)

OTHER PUBLICATIONS

Osborne, Geoffrey W. "A Method of Quantifying Cell Sorting Yield in 'Real Time'", Cytometry Part A, vol. 77A, No. 10, Jul. 26, 2010, pp. 983-989.

(Continued)

*Primary Examiner* — Rebecca Martinez
(74) *Attorney, Agent, or Firm* — Bret E. Field; Bozicevic, Field & Francis LLP

(57) ABSTRACT

Provided herein are improved cell sorter systems and methods. Such systems and methods provide a self-stabilizing sorter jet to automate calibration, and address the issue of drift in cell sorting systems. The systems and methods presented make it possible to determine and set the charge delay interval automatically with circuitry in the cell sorter. These circuits can set, monitor, and adjust the time delay continuously, allowing for a completely automatic, autonomous, turn-key, self-stabilizing sorter jet.

6 Claims, 3 Drawing Sheets

(56) References Cited

U.S. PATENT DOCUMENTS

| | | |
|---|---|---|
| 4,284,496 A | 8/1981 | Newton |
| 4,487,320 A | 12/1984 | Auer |
| 4,538,733 A | 9/1985 | Hoffman |
| 5,150,313 A | 9/1992 | Van den Engh et al. |
| 5,407,794 A | 4/1995 | Kass |
| 5,466,572 A | 11/1995 | Sasaki et al. |
| 5,475,487 A | 12/1995 | Mariella, Jr. et al. |
| 5,483,469 A | 1/1996 | Van den Engh et al. |
| 5,489,506 A | 2/1996 | Crane |
| 6,003,678 A | 12/1999 | Van den Engh |
| 6,211,477 B1 | 4/2001 | Cardott et al. |
| 6,589,792 B1 | 7/2003 | Malachowski |
| 7,639,358 B2 | 12/2009 | Kanda |
| 7,679,039 B2 | 3/2010 | Van den Engh et al. |
| 7,728,974 B2 | 6/2010 | Van den Engh |
| 2002/0034748 A1 | 3/2002 | Quake et al. |
| 2002/0053532 A1 | 5/2002 | Quake et al. |
| 2002/0119558 A1 | 8/2002 | Seidel et al. |
| 2002/0127144 A1* | 9/2002 | Mehta ............... G01N 15/1031 422/81 |
| 2002/0167656 A1 | 11/2002 | Van den Engh |
| 2002/0186375 A1 | 12/2002 | Asbury et al. |
| 2005/0042760 A1 | 2/2005 | Yount et al. |
| 2005/0112541 A1 | 5/2005 | Durack et al. |
| 2005/0258358 A1 | 11/2005 | Thakur |
| 2006/0002824 A1 | 1/2006 | Chang et al. |
| 2006/0263829 A1 | 11/2006 | Evans et al. |
| 2007/0117086 A1 | 5/2007 | Evans et al. |
| 2007/0269348 A1 | 11/2007 | Van den Engh et al. |
| 2008/0213915 A1 | 9/2008 | Durack et al. |
| 2009/0107893 A1 | 4/2009 | Schembri et al. |
| 2009/0176271 A1 | 7/2009 | Durack et al. |
| 2010/0297759 A1 | 11/2010 | Kanda |
| 2010/0314555 A1 | 12/2010 | Muraki |
| 2011/0020855 A1 | 1/2011 | Shinoda et al. |

FOREIGN PATENT DOCUMENTS

| | | |
|---|---|---|
| JP | H06281622 A | 10/1994 |
| JP | 11-337558 A | 12/1999 |
| JP | 2002521658 A | 7/2002 |
| JP | 2006194882 A | 7/2006 |
| JP | 2011-47753 A | 3/2011 |
| WO | WO 92/17288 A1 | 10/1992 |
| WO | WO 2010-095391 A1 | 8/2010 |

OTHER PUBLICATIONS

Petersen et al. "Stability of the Breakoff Point in a High-Speed Cell Sorter", Cytometry Part A, vol. 56A, No. 2, pp. 63-70 (2003).

* cited by examiner

CELL SORTER SYSTEM AND METHOD

CROSS-REFERENCE TO RELATED APPLICATIONS

Pursuant to 35 U.S.C. §119 (e), this application is a Divisional application of U.S. patent application Ser. No. 14/009,032 filed Nov. 5, 2013, which application is a 371 national phase filing of International Application No. PCT/US US2012/028951 filed Mar. 13, 2012, which application claims priority to the filing date of U.S. Provisional Patent Application Ser. No. 61/480,872 filed Apr. 29, 2011, the disclosures of which applications are herein incorporated by reference.

INTRODUCTION

The present invention relates to flow cytometers and instruments for high speed identification and sorting of particles, such as cells.

Flow cytometry is a valuable method for the analysis and isolation of biological particles such as cells and constituent molecules. As such it has a wide range of diagnostic and therapeutic applications. The method utilizes a fluid stream to linearly segregate particles such that they can pass, single file, through a detection apparatus. Individual cells can be distinguished according to their location in the fluid stream and the presence of detectable markers. Thus, a flow cytometer can be used to produce a diagnostic profile of a population of biological particles.

Isolation of biological particles has been achieved by adding a sorting or collection capability to flow cytometers. Particles in a segregated stream, detected as having one or more desired characteristics, are individually isolated from the sample stream by mechanical or electrical removal. This method of flow sorting has been used to sort cells of different types, to separate sperm bearing X and Y chromosomes for animal breeding, to sort chromosomes for genetic analysis, and to isolate particular organisms from complex biological populations.

A common flow sorting technique utilizes drop sorting in which a fluid stream containing linearly segregated particles is broken into drops and the drops containing particles of interest are electrically charged and deflected into a collection tube by passage through an electric field. Current drop sorting systems are capable of forming drops at a rate of 100,000 drops/second in a fluid stream that is passed through a nozzle having a diameter less than 100 micrometers. Drop sorting requires that the drops break off from the stream at a fixed distance from the nozzle tip. The distance is normally on the order of a few millimeters from the nozzle tip and can be maintained for an unperturbed fluid stream by oscillating the nozzle tip at a predefined frequency.

Typically, the linearly segregated particles in the stream are characterized as they pass through an observation point situated just below the nozzle tip. Once a particle is identified as meeting one or more desired criteria, the time at which it will reach the drop break-off point and break from the stream in a drop can be predicted. Ideally, a brief charge is applied to the fluid stream just before the drop containing the selected particle breaks from the stream and then grounded immediately after the drop breaks off. The drop to be sorted maintains an electrical charge as it breaks off from the fluid stream, and all other drops are left uncharged. The charged drop is deflected sideways from the downward trajectory of the other drops by an electrical field and collected in a sample tube. The uncharged drops fall directly into a drain.

Perturbations in a fluid stream, including turbulence caused by variability in the size of particles present in typical biological samples or drift in cytometer components can significantly impact the ability to predict which drop will contain a particle of interest. Improper prediction of which drop contains a particle can lead to loss of valuable particles which are often present in small amounts in biological samples. Even a brief lapse in the ability to accurately predict the contents of a drop can contaminate a fraction of desired particles with unwanted particles, thereby compromising the quality of the fraction or rendering it unfit for therapeutic administration.

Although diagnostic flow cytometers have been made available for common use in a variety of settings, flow sorting is more complicated and has been confined primarily to core facilities having dedicated operators. Currently flow sorters require relatively complicated setup and alignment procedures that often necessitate highly trained operators. While flow analyzers have seen many improvements towards ease of use due to automation and simplification, most of the improvements in flow sorters have been directed to increasing sort speed and the number of parameters used. The increases in speed and number of parameters have had the effect of increasing the complexity and precision required in flow sorters.

For example, in a typical cell sorter system, an operator needs to accurately set the delay time between an event (e.g., the detection of a cell) at the intersect of a laser and a jet stream (i.e., laser-jet-intersect (LJI)), and the application of a charge pulse to the jet. The charge pulse must overlap the point in time when the drop that contains the measured cell separates from the main jet at the break-off point (BOP). Currently this adjustment of the time delay is done manually before the sort, making the accuracy and purity of sorting dependent on subjective criteria. In addition, because the time delay is adjusted before the sort it is prone to drift due to pressure and temperature changes that occur over the duration of the sort.

SUMMARY

Provided herein are improved cell sorter systems and methods. Such systems and methods provide a self-stabilizing sorter jet to automate calibration and address the issue of drift in cell sorting systems. The systems and methods presented make it possible to determine and set the charge delay interval (CDI) automatically with circuitry in the cell sorter. These circuits can set, monitor, and adjust the time delay continuously, allowing for a completely automatic, autonomous, turn-key, self-stabilizing sorter jet.

Presented herein are also systems and methods for automatically determining the phase of the break off point of the jet (PBP), making it possible to know when the drop with the cell separates from the jet. By combining the presented systems and methods with methods for automatically determining the phase of the drop drive signal when an event (e.g., cell) passes the intersection point of the laser and the jet of a cell sorter (as described in U.S. Pat. No. 7,679,039, which is herein incorporated by reference in its entirety), the distance between measurement point (e.g., at the LJI) and the jet break-off point (BOP) can be set and maintained at a whole number (n) of drops.

For example, presented are methods for determining n once LJI and BOP have been fixed. All calculations can be done with circuitry that perform phase and distance sensing inside a closed feed-back loop. The combination of inventions described here allow, for the first time, the construction of an apparatus that can automatically and autonomously set its break-off point, drop delay, and the timing pulse charge signal. Because the calculations are done inside a feedback loop, such a system is stable and autonomously corrects for changes in temperature and pressure.

In one exemplary embodiment, to measure the time of the BOP, first, the drain that collects the droplet stream is insulated. Next, the drain is connected with a current to voltage converter (CVC) to ground. With the deflection plates turned off, a charge is placed on the droplet stream. The charge will be carried by the drops to the drain. The charge will flow to ground through the CVC circuit, generating a voltage read out in the circuit. Drops will only carry charge if there was a voltage applied to the jet at the time the drop separates from the jet. If a charge is placed onto the stream as a very short pulse, the duration of which only occupies a fraction of the drop cycle period, the stream of drops will only carry a charge if the charge pulses coincide with the break-off timing of the drops. The amplitude of the drop drive signal can now be adjusted such that the drop break-off point and the jet laser intersection point are separated by a whole number of drop cycles (the LJI signal and the charge pulse are in sync with zero phase difference) by periodically performing this procedure: (1) disengage deflection plates; (2) apply flash charge in sync with signal at the laser jet intersection point; and (3) adjust drive amplitude for maximum drain current.

The instrument can automatically and rapidly adjust its drop drive amplitude such that the time between event measurement and drop formation remains constant. Once the drop break-off is in sync with the drop-drive frequency at the LJI point, the length of the time interval between an event measurement and the break off point must be determined. In one embodiment, the drop drive is set at a preferred frequency $f_1$. The time delay between the event measurement and the flash charge is kept constant ($\partial t$). The drop drive frequency is increased while keeping the drop amplitude constant until the charge pulse again coincides with the BOP (can be detected by observing the drain current). The frequency at which this happens, $f_2$ is noted. The following relationships must hold:

$$\partial t = n/f_1$$

$$\partial t = (n+1)/f_2$$

The number of drop cycles, n, between LJI and BOP therefore must be:

$$n = f_1/(f_2 - f_1)$$

All relevant signals can be adjusted by computer or may be held constant in closed feedback loops. Therefore all properties of the jet can be kept constant by circuitry in the instrument. To make the method more accurate the automatic delay calculation can be done at multiple frequencies, for instance those for n−2, n−1, n+1, and n+2. An accurate value of n can be determined by a regression analysis.

BRIEF DESCRIPTION OF THE FIGURES

The accompanying drawings, which are incorporated herein, form part of the specification. Together with this written description, the drawings further serve to explain the principles of, and to enable a person skilled in the relevant art(s), to make and use systems and methods in accordance with the present invention.

DETAILED DESCRIPTION

The following detailed description of the figures refers to the accompanying drawings that illustrate an exemplary embodiment of a cell sorter system. Other embodiments are possible. Modifications may be made to the embodiment described herein without departing from the spirit and scope of the present invention. Therefore, the following detailed description is not meant to be limiting.

Figure 1:
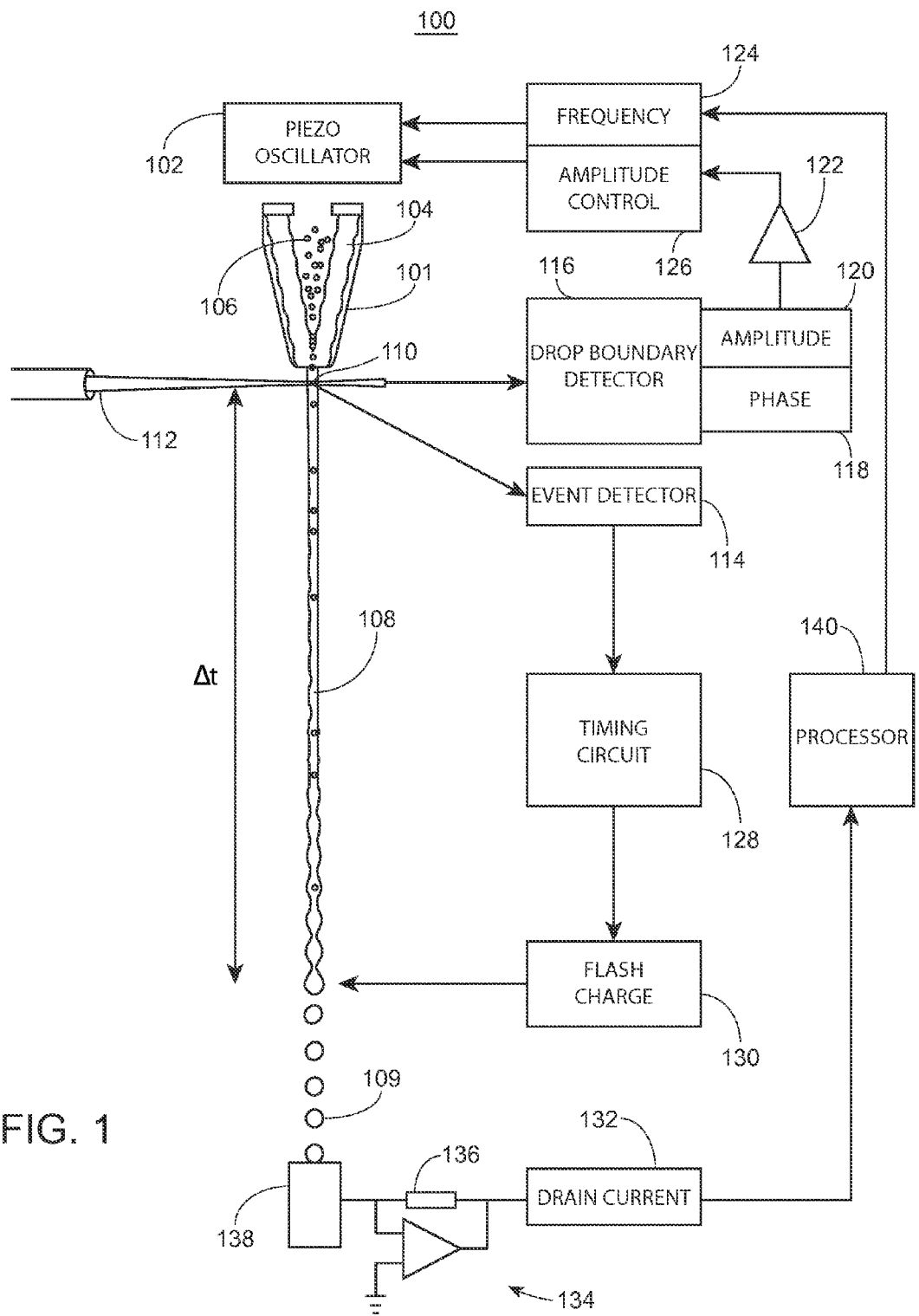
FIG. 1 is a schematic drawing of a cell sorter system.

FIG. 1 is a schematic drawing of a cell sorter system 100, in accordance with one embodiment presented herein. As shown in FIG. 1, a drop formation transducer (e.g., piezo-oscillator) 102 is coupled to a fluid conduit, such as nozzle 101. Within nozzle 101, sheath fluid 104 hydrodynamically focuses a sample fluid 106 into a stream 108. Within stream 108, particles (e.g., cells) are lined up in single file to cross a laser-stream intersect 110 (e.g., the LJI), irradiated by an irradiation source (e.g., laser) 112. Vibration of piezo-oscillator 102 causes stream 108 to break into a plurality of drops 109.

In operation, an event detector 114 identifies when a particle of interest (or cell of interest) crosses laser-stream intersect 110. Event detector 114 feeds into timing circuit 128, which in turn feeds into flash charge circuit 130. At the drop break off point, informed by a timed drop delay ($\Delta t$), a flash charge is applied to the stream such that the drop of interest carries a charge. The charged drop can then be sorted by activating deflection plates (not shown) to deflect the drop into a collection tube. As shown in FIG. 1, however, the drops are collected in a drain receptacle 138.

Drop boundary detector 116 serves to automatically determine the phase of the drop drive signal when a particle of interest passes the laser-stream intersect 110. An exemplary drop boundary detector is described in U.S. Pat. No. 7,679,039, which is incorporated herein by reference in its entirety. Drop boundary detector 116 allows the instrument to accurately calculate the place of each detected particle in a drop. Drop boundary detector 116 feeds into an amplitude signal 120 and phase 118 signal, which in turn feeds (via amplifier 122) into an amplitude control circuit 126 and/or frequency control circuit 124. Amplitude control circuit 126 and/or frequency control circuit 124, in turn, controls piezo-oscillator 102.

Cell sorter system 100 further includes a current-to-voltage converter (CVC) 134 coupled to receptacle 138. CVC 134 is configured to detect the presence of a charged particle entering receptacle 138. Resistor 136 sets the volts-per-amp of CVC 134, and provides a voltage that is proportional to current observed at receptacle (e.g., drain) 138. Drain current is measured in circuit unit 132 and is provided to a processor 140. Processor 140 then feeds into frequency control circuit 124.

Cell sorter system 100 may be employed to provide a self-stabilizing sorter jet to automate calibration, and address the issue of drift in cell sorting systems. The system makes it possible to determine and set the charge delay interval automatically with the presented circuitry. These circuits can set, monitor, and adjust the time delay continuously, allowing for a completely automatic, autonomous, turn-key, self-stabilizing sorter jet. Cell sorter system 100 may be used in various ways, such as in the practice of the methods further outlined below.

In another embodiment, there is provided a cell sorter system, the system comprising: a fluid conduit; an irradiation source positioned to irradiate a fluid stream present in the fluid conduit; a charge circuit providing an electrical charge to the fluid stream; a receptacle positioned to receive one or more drops formed from the fluid stream; and a current detection circuit coupled to the receptacle. The system may further include a charge delay control unit controlling the charge circuit, wherein the charge delay control unit receives a signal from the current detection circuit and determines a charge delay based on the signal received from the current detection circuit. The system may further comprise a current-to-voltage converter to detect the presence of a charged drop entering the receptacle. The system may further comprise an integrator to detect a number of drops per unit time entering the receptacle. In one embodiment, the receptacle is a drain. The drain may be electrically insulated. In another embodiment, the receptacle is a drop collection tube. The drop collection tube may be electrically insulated.

In still another embodiment, there is provided a charge delay control system for a flow cytometer, the system comprising: a charge circuit providing an electrical charge to a fluid stream in the flow cytometer; a current detection circuit coupled to a receptacle, wherein the receptacle is positioned to receive one or more drops formed from the fluid stream; and a charge delay control unit operatively coupled to the current detection circuit, wherein the charge delay control unit is configured to determine a charge delay based on a current measured by the current detection circuit. The system may further include: a current-to-voltage converter to detect the presence of a charged drop entering the receptacle; and/or an integrator to detect a number of drops per unit time entering the receptacle. The charge delay control unit may be further configured to: (a) apply a flash charge to the fluid stream at a first drive frequency of a drop formation transducer of the flow cytometer; (b) identify an optimal drive amplitude by varying a drive amplitude of the drop formation transducer until a maximum current is detected at the receptacle; (c) identify a second drive frequency by increasing the drive frequency of the drop formation transducer, while continuing to apply the flash charge at the first drive frequency, until the current measured at the receptacle returns to the maximum current; and/or (d) calculate a drop delay based on the first and second drive frequencies.

Figure 2:
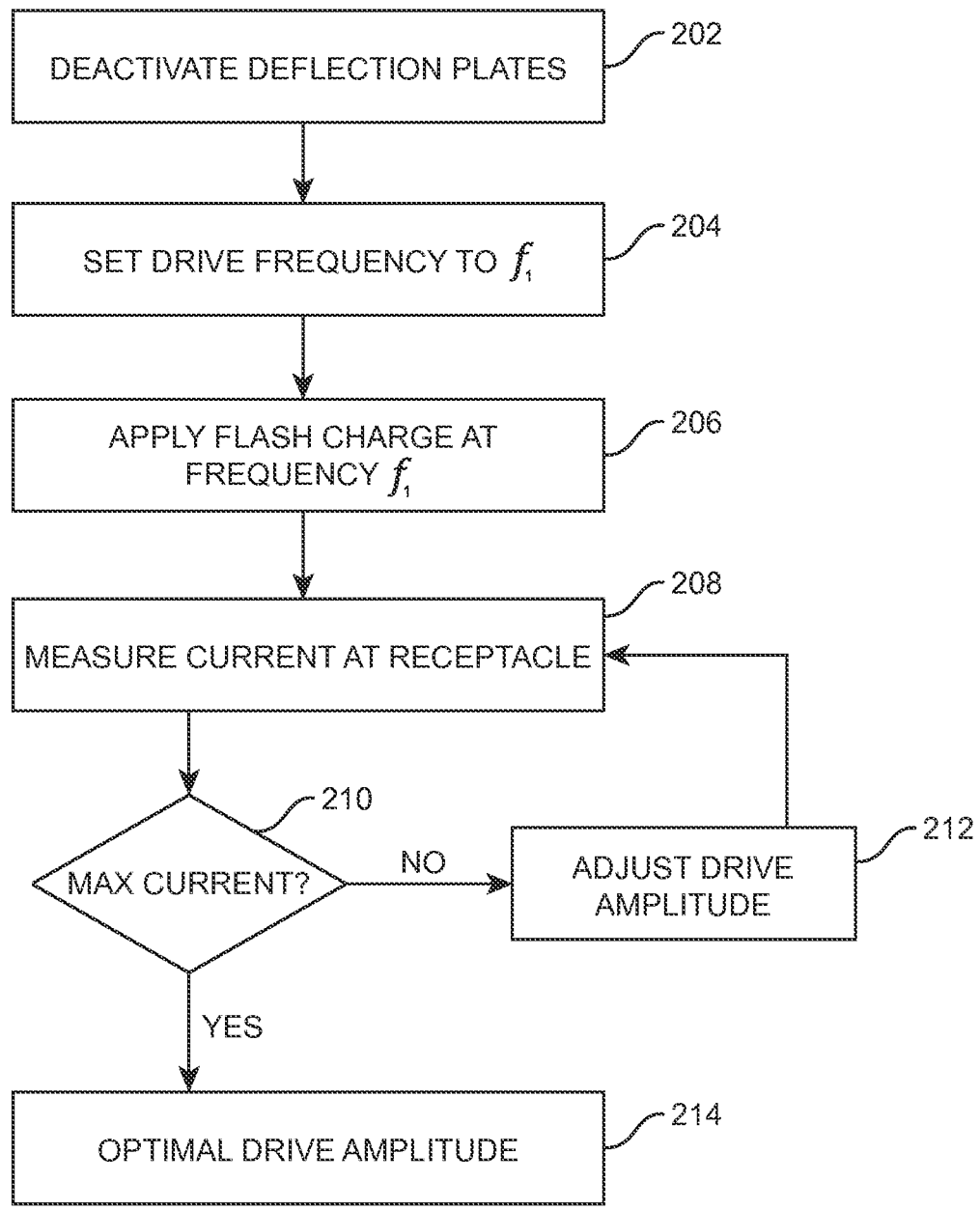
FIG. 2 is a flowchart outlining a method, in accordance with one embodiment presented herein.

FIG. 2 is a flowchart outlining an exemplary method 200 for calibrating a cell sorter, and more specifically for determining an optimal drive amplitude for an oscillator coupled to a fluid nozzle. In step 202, any deflection plates are deactivated. Step 202 is an optional step for simplification of the method presented. Alternative methods may be employed with deflection plates activated. In step 204, the drive frequency of the oscillator unit is set to a constant frequency ($f_1$). A flash charge is applied to the stream at the frequency ($f_1$), in step 206. Current is then measured at a receptacle, in step 208. If the current measured over time is a maximum (or peak) current, the amplitude is identified and as an optimal drive amplitude, as in step 214. However, if the current measured at the receptacle is not a maximum (or peak) current, the drive amplitude is adjusted, in step 212, and step 208 is repeated until an optimal drive amplitude is identified.

Figure 3:
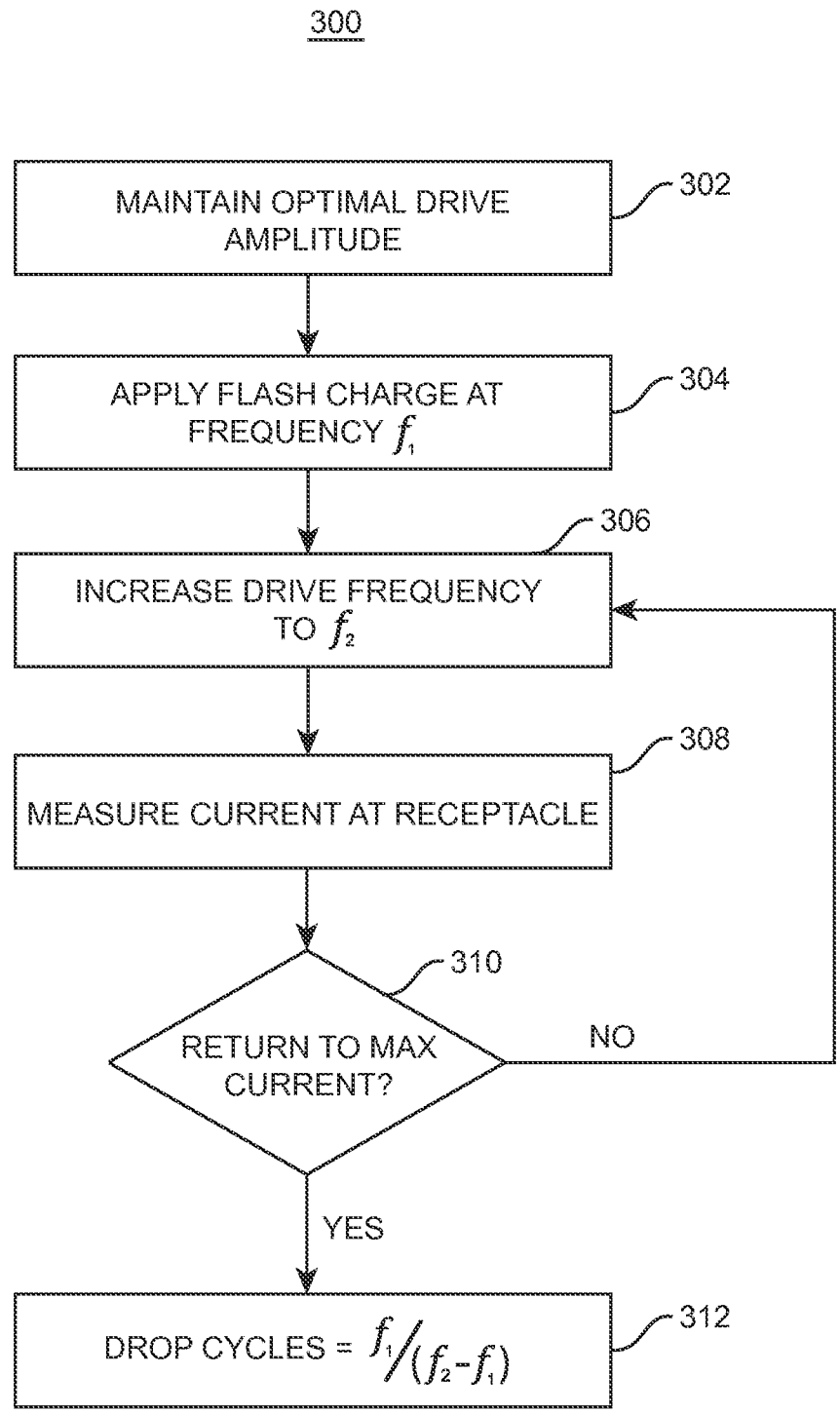
FIG. 3 is a flowchart outlining a method, in accordance with one embodiment presented herein.

FIG. 3 is a flowchart outlining an exemplary method 300 for calibrating a cell sorter, and more specifically for determining the drop cycles and/or optimal drive frequency for an oscillator unit. In step 302, the optimal drive amplitude (such as identified in step 214) is maintained constant. In step 304, a flash charge is applied at frequency ($f_1$). The drive frequency is then increased to frequency ($f_2$), in step 306. Current is again measured at the receptacle, in step 308. In step 310, a determination is made as to whether the current measured at the receptacle has returned to the "maximum current," i.e., returned to the current seen when the drive frequency was $f_1$. Until the current returns to a maximum, the drive frequency is continuously adjusted to a higher frequency, $f_2$. When a maximum current is once again detected at the receptacle, the drop cycles is calculated as a function of $(f_1)/(f_2-f_1)$.

In another embodiment, there is provided a method for calibrating a cell sorter system, the method comprising: (a) setting a drive frequency of a drop formation transducer; (b) applying a flash charge to the fluid stream at the drive frequency; (c) measuring a current at a receptacle receiving formed droplets from the fluid stream; and (d) identifying an optimal drive amplitude by varying the drive amplitude of the drop formation transducer until a maximum current is detected at the receptacle. The method may further include (e) identifying a second drive frequency by increasing the drive frequency of the drop formation transducer, while continuing to apply the flash charge at the drive frequency of step (a), until the current measured at the receptacle returns to the maximum current. The method may further include: (1) calculating a drop delay based on the drive frequency identified in step (e) and the drive frequency of step (a); (2) maintaining the drive amplitude of the drop formation transducer constant at the optimal drive amplitude; (3) deactivating a deflection plate prior to step (a); and/or (4) electrically insulating the receptacle.

In one embodiment, there is provided a method of synchronizing a cell sorter's drive frequency with the drop formation (or break-off) frequency. The "drive frequency" is the frequency at which the transducer (e.g., piezo-element) is driven. The "drop formation frequency" or "break-off frequency" is the frequency at which the drops actually break off from the stream. The drive frequency and drop formation frequency may become out of sync due to external factors (e.g., changes in temperature, pressure, etc.). However, when the drive frequency and the drop formation frequency are in sync, there are a whole number of drops between the laser-jet-intersect (LJI) and the break-off point (BOP). The system's drive frequency is a "known" (i.e., set) variable, but the drop formation frequency is an "unknown" (i.e., subject to external fluctuations) variable.

An exemplary method to synchronize the drive frequency with the drop formation frequency comprises: (a) (if necessary) the deflection plates are turned off; (b) a flash charge is applied to the stream at the drive frequency ($f_1$); (c) with the drive frequency and the charge frequency held constant at $f_1$, the drive amplitude is varied. By changing the drive amplitude while maintaining the drive frequency constant, the drop formation frequency is varied. When a maximum drain current is measured with the modified drain (or collection tube), then it is known that an optimal drive amplitude has been achieved.

Next, the drop delay is determined. To determine the drop delay: (1) the drive amplitude is maintained constant at the optimal drive amplitude determined in step (c) above; (2) with the charge frequency held constant at $f_1$, the system's drive frequency is increased until a maximum current reappears at the drain, which is at a drive frequency $f_2$; (3) the number of drops between the LJI and the BOP is $n=f_1/(f_2-$ $f_1$); (4) then the drop delay is calculated based on the number of drops between the LJI and the BOP.

CONCLUSION

The foregoing description of the invention has been presented for purposes of illustration and description. It is not intended to be exhaustive or to limit the invention to the precise form disclosed. Other modifications and variations may be possible in light of the above teachings. The embodiments were chosen and described in order to best explain the principles of the invention and its practical application, and to thereby enable others skilled in the art to best utilize the invention in various embodiments and various modifications as are suited to the particular use contemplated. It is intended that the appended claims be construed to include other alternative embodiments of the invention; including equivalent structures, components, methods, and means.

It is to be appreciated that the Detailed Description section, and not the Summary and Abstract sections, is intended to be used to interpret the claims. The Summary and Abstract sections may set forth one or more, but not all exemplary embodiments of the present invention as contemplated by the inventor(s), and thus, are not intended to limit the present invention and the appended claims in any way.

It is to be understood that this invention is not limited to particular embodiments described, as such may, of course, vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limit of that range and any other stated or intervening value in that stated range, is encompassed within the invention. The upper and lower limits of these smaller ranges may independently be included in the smaller ranges and are also encompassed within the invention, subject to any specifically excluded limit in the stated range. Where the stated range includes one or both of the limits, ranges excluding either or both of those included limits are also included in the invention.

Certain ranges are presented herein with numerical values being preceded by the term "about." The term "about" is used herein to provide literal support for the exact number that it precedes, as well as a number that is near to or approximately the number that the term precedes. In determining whether a number is near to or approximately a specifically recited number, the near or approximating unrecited number may be a number which, in the context in which it is presented, provides the substantial equivalent of the specifically recited number.

Unless defined otherwise, all technical and scientific terms used herein have the same meaning as commonly understood by one of ordinary skill in the art to which this invention belongs. Although any methods and materials similar or equivalent to those described herein can also be used in the practice or testing of the present invention, representative illustrative methods and materials are now described.

All publications and patents cited in this specification are herein incorporated by reference as if each individual publication or patent were specifically and individually indicated to be incorporated by reference and are incorporated herein by reference to disclose and describe the methods and/or materials in connection with which the publications are cited. The citation of any publication is for its disclosure prior to the filing date and should not be construed as an admission that the present invention is not entitled to antedate such publication by virtue of prior invention. Further, the dates of publication provided may be different from the actual publication dates which may need to be independently confirmed.

It is noted that, as used herein and in the appended claims, the singular forms "a", "an", and "the" include plural referents unless the context clearly dictates otherwise. It is further noted that the claims may be drafted to exclude any optional element. As such, this statement is intended to serve as antecedent basis for use of such exclusive terminology as "solely," "only" and the like in connection with the recitation of claim elements, or use of a "negative" limitation.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable sub-combination. All combinations of the embodiments are specifically embraced by the present invention and are disclosed herein just as if each and every combination was individually and explicitly disclosed, to the extent that such combinations embrace operable processes and/or devices/systems/kits. In addition, all sub-combinations listed in the embodiments describing such variables are also specifically embraced by the present invention and are disclosed herein just as if each and every such sub-combination of chemical groups was individually and explicitly disclosed herein.

As will be apparent to those of skill in the art upon reading this disclosure, each of the individual embodiments described and illustrated herein has discrete components and features which may be readily separated from or combined with the features of any of the other several embodiments without departing from the scope or spirit of the present invention. Any recited method can be carried out in the order of events recited or in any other order which is logically possible.

What is claimed is:

1. A method for calibrating a cell sorter system, the method comprising:
   (a) setting a drive frequency of a drop formation transducer;
   (b) applying a flash charge to a fluid stream at the drive frequency;
   (c) measuring a current at a receptacle receiving formed droplets from the fluid stream with a current detection circuit coupled to the receptacle; and
   (d) identifying an optimal drive amplitude by varying the drive amplitude of the drop formation transducer until a maximum current is detected at the receptacle.

2. The method of claim 1, further comprising:
   (e) identifying a second drive frequency by increasing the drive frequency of the drop formation transducer, while continuing to apply the flash charge at the drive frequency of step (a), until the current measured at the receptacle returns to the maximum current.

3. The method of claim 2, further comprising:
   calculating a drop delay based on the drive frequency identified in step (e) and the drive frequency of step (a).

4. The method of claim 2, further comprising:
maintaining the drive amplitude of the drop formation transducer constant at the optimal drive amplitude.

5. The method of claim 1, further comprising:
deactivating a deflection plate prior to step (a).

6. The method of claim 1, further comprising:
electrically insulating the receptacle.

* * * * *